United States Patent [19]

Silver et al.

[11] Patent Number: 5,230,696
[45] Date of Patent: Jul. 27, 1993

[54] POLYCENTRIC VARIABLE AXIS HINGE FOR AN ORTHOPEDIC KNEE BRACE

[76] Inventors: Daniel M. Silver, 231 N. Rockingham Ave., Los Angeles, Calif. 90049; Richard Nauert, 861 Production Pl., Newport Beach, Calif. 92663; Russell A. Rothenberg, 4267 Marina City Dr., Suite 1014, West Tower South, Marina del Rey, all of Calif. 90292

[21] Appl. No.: 915,533

[22] Filed: Jul. 20, 1992

[51] Int. Cl.$^5$ ............................................. A61F 5/00
[52] U.S. Cl. .............................. 602/16; 602/26; 623/37
[58] Field of Search ............... 602/16, 26; 623/39; 126/60 C

[56] References Cited

U.S. PATENT DOCUMENTS

| | | | |
|---|---|---|---|
| 4,361,142 | 11/1982 | Lewis et al. | 128/80 |
| 4,463,751 | 8/1984 | Bledsoe | 128/80 |
| 4,573,455 | 3/1986 | Hoy | 128/80 |
| 4,699,129 | 10/1987 | Aaserude et al. | 128/80 |
| 4,732,143 | 3/1988 | Kausek et al. | 602/16 |
| 4,773,404 | 9/1988 | Townsend | 128/80 |
| 4,821,707 | 4/1989 | Audette | 128/80 |
| 4,890,607 | 1/1990 | Townsend | 128/80 |
| 4,940,044 | 7/1990 | Castillo | 602/16 |
| 5,009,223 | 4/1991 | DeFonce | 128/80 |
| 5,107,824 | 4/1992 | Rogers et al. | 602/16 |

FOREIGN PATENT DOCUMENTS 2600528 12/1987 France ............................ 128/80 C Primary Examiner—Robert Bahr
Assistant Examiner—Beverly A. Meindl
Attorney, Agent, or Firm—Keith D. Beecher

[57] ABSTRACT

A polycentric variable axis hinge for use in an orthopedic knee brace to provide a mechanical joint between the femoral and tibial cuffs of the brace. The hinge includes a femoral stem which is attached to the femoral cuff and which extends downwardly from the femoral cuff, and it also includes a tibial stem attached to the tibial cuff and extending upwardly from the tibial cuff. The ends of the two stems overlap one another to provide a joint. The distal end of the femoral stem has first and second variable radii slots formed in it, the slots being positioned one above the other and extending in the anterior-posterior direction, and the lower slot being longer than the upper slot. A first bearing pin is mounted on the distal end of the tibial stem, and it is received in the upper slot. Two additional bearing pins are mounted on the distal end of the tibial stem and are received in the lower slot. The action is such that angular movement of the stems relative to one another causes them to slide, glide and rotate relative to one another to replicate the actual movement of the knee joint of the user as the leg is bent and straightened.

3 Claims, 1 Drawing Sheet

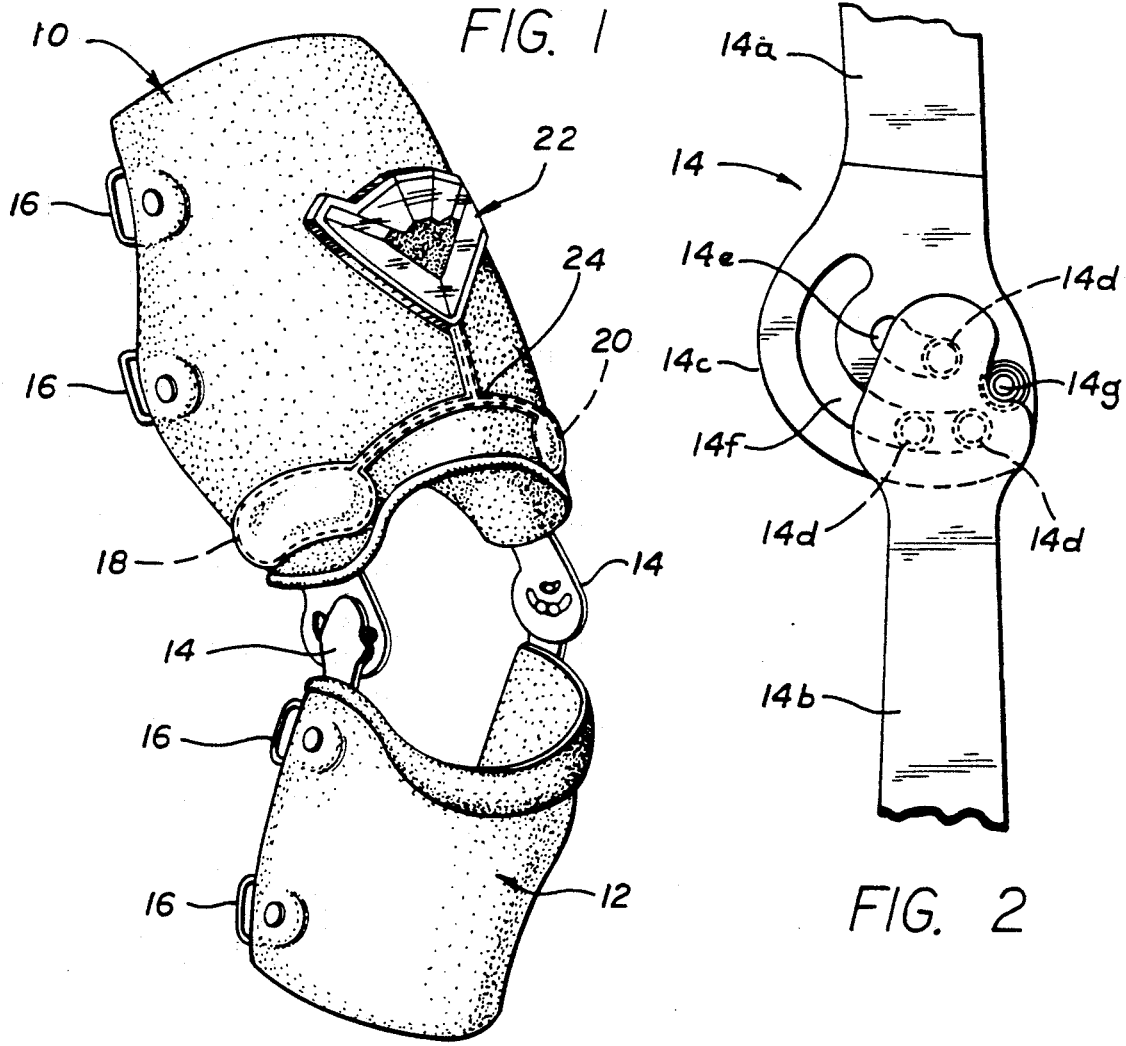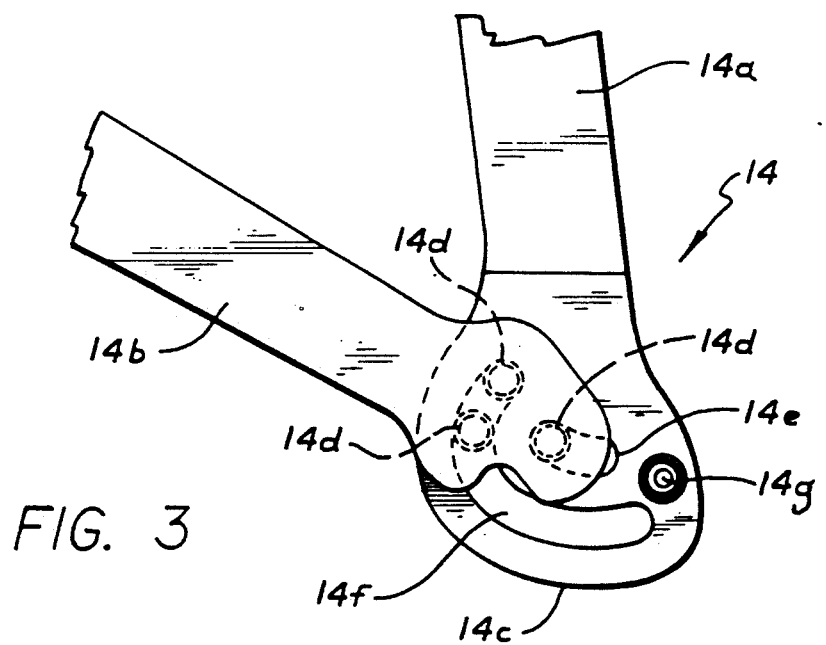

POLYCENTRIC VARIABLE AXIS HINGE FOR AN ORTHOPEDIC KNEE BRACE

BACKGROUND OF THE INVENTION

The present invention relates to a polycentric variable axis hinge for use, in particular, but not exclusively, in knee braces intended to reinforce an injured knee joint.

The human knee is acknowledged as one of the weakest joints in the body. It is the articulating joint between the thigh and calf muscle groups, and it supports the weight of the body while a person is walking or running. The joint is held together by two small but strong ligaments, namely, the anterior and posterior cruciate ligaments. Knee instability arising out of cartilage damage, the ligament strain and other causes is relatively commonplace since the knee joint is subjected to significant loads during the course of almost any kind of physical activity requiring the use of the legs.

The thigh and legs of the human body are articulated to each other through the knee joint of which the principal motions are extension and flexion by rotation about a horizontal axis extending across the knee in a medial-lateral direction. These motions are complex because they take place about a rotational axis which is not fixed, as is the case with the elbow, but which shifts slightly across the knee in the anterior-posterior direction.

It is important for an adequate knee brace to follow the shifting path of the rotational axis of the knee as closely as possible, and accordingly the principal objective of the present invention is to provide a knee brace hinge which is capable of fulfilling such a criterion.

Additionally, and particularly in the case of injured or weak knees, means must be provided in the hinge of the knee brace to control the extension of the knee joint and to stop the extension, for example, short of 15%–5% of full extension, so as to prevent of knee ligaments injuries. Another objective of the invention is to provide a knee brace hinge, which incorporates improved stop means that may be adjustable to tailor the hinge to individuals, to control the extension of the knee joint and to stop the extension at a predetermined degree of full extension.

In U.S. Pat. No. 4,773,404, and its parent U.S. Pat. No. 4,723,539, and in U.S. Pat. No. 4,890,607, a multi-axis controlled motion knee hinge is disclosed. The hinge is constructed to constrain the tibia to slide rearwardly relative to the femur for a predetermined distance throughout an initial range of flexion of the knee from a straight leg position, and beyond that initial range of flexion, to rotate relative to the femur along a predetermined arcuate path.

In the construction of the hinge described in U.S. Pat. No. 4,890,607, the end portions of femoral and tibial lengths are interconnected by a cam assembly comprised of a pair of cam slots in one of the links and cam follower pins mounted on the other link and engaging the slots. In the particular construction described in U.S. Pat. No. 4,890,607, each slot has a straight segment adjoining an arcuate segment of equal radius. The variable axis hinge of the present invention is of the same general type as the hinge disclosed in U.S. Pat. No. 4,890,607, but it is constructed in a manner such that the hinge more closely follows the actual movement of the knee, as the leg is bent in the rearward direction.

Accordingly, a general objective of the present invention is to provide an improved multi-axis controlled hinge for an orthopedic knee brace which is constructed to have the ability accurately to replicate the complex movements of the knee of a wearer, as the leg is moved.

Another objective of the invention is to provide such an improved multi-axis hinge having relatively high integral strength, as well as tolerance precision and production efficiency.

Yet another objective of the invention is to provide such a variable axis knee brace hinge which is constructed in a manner that enables integration into the hinge of a stop for limiting the range of movement of the leg, and one which may be tailored for individual wearers.

The foregoing objects of the invention are achieved in accordance with a preferred embodiment, wherein a knee brace hinge mechanism is provided which utilizes first and second variable radii camming slots and corresponding cam pin followers, wherein one of the camming slots serves to provide the anterior motion of the upper portion of the hinge, while the second camming slot provides for the unicentric phase of the hinge artarokinematics. During the initial range of motion, pivoting occurs through a short multi-radii slot segment about one of the cam pin followers disposed within that slot. After that cam pin follower reaches the anterior end of the slot, it serves as the axis of rotation or pivot point for movement of other cam pin followers along the second variable radii slot. Such a construction provides an increase in tolerance precision, a precise following of the complex motion of the knee joint, and forceful action of the hinge through the entire range of motion.

BRIEF DESCRIPTION OF THE DRAWINGS

FIG. 1 is a perspective representation of a portion of an orthopedic knee brace which includes an upper anterior cuff and a lower anterior cuff, the upper and lower cuffs being hinged together by a pair of polycentric variable axis hinges which may be constructed in accordance with the concepts of the invention;

FIG. 2 is a schematic representation of one of the polycentric variable axis hinges incorporating the concepts of the invention, showing the position of the hinge when the leg of the wearer is fully extended; and FIG. 3 is a schematic representation of the hinge showing the position of the hinge when the leg of the wearer is bent to an extreme bent position.

DETAILED DESCRIPTION OF THE ILLUSTRATED EMBODIMENT

As stated above, FIGURE I is a perspective representation of a portion of an orthopedic knee brace which includes an upper anterior cuff 10 which engages the thigh of the wearer, and a lower anterior cuff 12 which engages the leg of the wearer below the knee. The upper and lower cuffs are hinged to one another by a pair of hinges 14 which, as stated, may be constructed to incorporate the concepts of the present invention.

In the embodiment shown in FIG. 1, a pair of air pillows 18 and 20 are interposed between a band 16 and the thigh of the wearer in accordance which the concepts disclosed in Copending application Ser. No. 07/911,738, filed Jul. 10, 1992, in the name of the present inventors, and which is assigned to the present assignee. As described in the copending application, the air pillows may be inflated by a miniature air pump 22 which enables the wearer, by repeatedly depressing and releasing the resilient top of the pump to introduce pressurized air into the air pillows through a tube 24. The air pillows are constructed and positioned to prevent the upper cuff 10 from sliding downwardly along the thigh of the wearer.

Details of the hinge 14 are shown in FIGS. 2 and 3. As shown, the hinge includes a femoral stem 14a which is securely joined to the femoral cuff 10 so as to project downwardly therefrom. The hinge also includes a tibial stem 14b which is securely attached to the tibial cuff 12 so as to extend upwardly from the tibial cuff. Any known means for joining the stems 14a and 14b to their respective cuffs may be utilized, such as laminating or sewing the stems into the cuffs. As can be seen from FIG. 1, the femoral and tibial stems 14a, 14b extend essentially parallel to each other and are positioned so that the distal ends thereof overlap to create a mechanical pivotal hinge mechanism 14c.

As shown in FIGS. 2 and 3, the hinge mechanism includes partially threaded bearing pins 14d which are threaded to the end of the tibial stem 14b, and which extend through slots 14e and 14f in the end of the femoral stem 14a. Slot 14e is positioned within the confines of slot 14f. The slots 14e and 14f also have variable radii so that angular and lateral movements of the stems 14a and 14b may be realized which precisely follow the angular movements of the femur and tibia of the wearer. As shown, one of the bearing pins 14d is received in upper slot 14e, and two of the bearing pins 14d are received in lower slot 14f. The three bearing pins 14d are positioned on the tibial stem 14b to form an isosceles triangle, as shown. The bearing pins 14d are self-lubricating, and function as cam followers in the slots 14e and 14f.

It will be observed that as of the tibial stem 14b is turned from the fully extended position of FIG. 2 to the bent position of FIG. 3, the upper bearing pin 14d moves in the slot 14e from one end to the other of the slot. During such movement, the tibial stem moves in a posterior direction with respect to the femoral stem.

When the upper bearing pin 14d reaches the end of the variable radii slot 14e, as shown in FIG. 3, the the tibial stem rotates about the axis of the upper bearing pin 14d until it reaches the extreme bent position show in FIG. 3, where the left hand lower bearing pin 14d engages the opposite end of the variable radius slot 14f.

Accordingly, as the wearer's leg is bent about the knee, the tibial and femoral stems 14b and 14a slide and glide and rotate in exactly the same manner as the knee.

An extension stop 14g is threaded into the end of the femoral stem 14a, to be engaged by a notched portion in the end of the tibial stem 14b when the leg of the wearer is fully extended. The stop 14g is provided with a rubber bushing so as to provide a soft cushioned stop for the mechanism when the leg is fully extended. The stop 14g is removable, and may be replaced by stops of different sizes, so as to tailor the hinge to the requirements of the individual user.

The invention provides, therefore, an improved polycentric variable axis hinge for an orthopedic knee brace which is constructed to follow precisely the movements of the wearer's knee as the leg is bent and straightened.

While a particular embodiment of the invention has been shown and described, modifications may be made. It is intended in the claims to cover all modifications which come within the true spirit and scope of the invention.

We claim:

1. A polycentric variable access hinge for use in an orthopedic knee brace providing a mechanical joint between the femoral and tibial cuffs of the brace, said hinge including a femoral stem attached to the femoral cuff and extending downwardly therefrom and a tibial stem attached to the tibial cuff and extending upwardly therefrom, with the distal ends of the stems overlapping one another to provide a joint, and with the distal end of said femoral stem having first and second variable radii slots formed therein positioned one above the other and extending in the anterior-posterior direction with the lower slot being longer than the upper slot and with the upper slot being positioned within the confines of the lower slot; a first bearing pin mounted on the distal end of the tibial stem and received in the upper slot in position to move in the upper slot from one end to the other of the upper slot during initial angular movement of said tibial stem as said tibial stem is turned from an extended position to a bend position with respect to said femoral stem, and said tibial stem rotating about the axis of said first bearing pin for the remainder of the angular movement of said tibial stem; and two additional bearing pins mounted on the distal end of the tibial stem and received in the lower slot, the additional bearing pins being disposed on isosceles triangular relationship with respect to the first-named bearing pin so that angular movement of the stems relative to one another causes the stems to slide and glide and rotate relative to one another to replicate the movements of the knee joint of the user as the leg is turned about the knee joint.

2. The polycentric variable axis hinge defined in claim 1, and which includes a removable stop member mounted on the distal end of said femoral stems to be engaged by the edge of the distal end of said tibial stems when the leg of the user is extended said stop serving to limit the extension angle of the leg.

3. The polycentric variable axis hinge defined in claim 2, in which said stop member includes a resilient busing to be engaged by the edge of the tibial stem to provide a soft stop therefor.

* * * * *